United States Patent [19]
Jeevanandam et al.

[11] Patent Number: 5,807,388
[45] Date of Patent: Sep. 15, 1998

[54] MYOCARDIAL REVASCULARIZATION THROUGH THE ENDOCARDIAL SURFACE USING A LASER

[75] Inventors: Valluvan Jeevanandam, New Milford, N.J.; Craig R. Smith, Bronxville, N.Y.

[73] Assignee: The Trustees of Columbia University in the City of New York, New York, N.Y.

[21] Appl. No.: 479,106

[22] Filed: Jun. 7, 1995

Related U.S. Application Data

[62] Division of Ser. No. 249,091, May 25, 1994, Pat. No. 5,607,421.

[51] Int. Cl.$^6$ ........................................................ A61N 5/02
[52] U.S. Cl. .................................. 606/15; 606/3; 606/7; 606/10
[58] Field of Search .................. 606/2, 3–17; 604/14–21; 128/897, 665, 666

[56] References Cited

U.S. PATENT DOCUMENTS

| | | | |
|---|---|---|---|
| 4,207,874 | 6/1980 | Choy | 606/7 |
| 4,431,005 | 2/1984 | McCormick | 128/665 |
| 4,469,098 | 9/1984 | Davi | 607/89 |
| 4,567,882 | 2/1986 | Heller | 604/21 |
| 4,862,887 | 9/1989 | Weber et al. | 606/7 |

FOREIGN PATENT DOCUMENTS

| | | | |
|---|---|---|---|
| 189329 | 7/1986 | European Pat. Off. | 606/7 |

*Primary Examiner*—David M. Shay
*Attorney, Agent, or Firm*—John P. White; Peter J. Phillips; Cooper & Dunham LLP

[57] ABSTRACT

Myocardial revascularization is performed by an apparatus and method which forms channels in the myocardium from inside the ventricular cavity without penetrating the full thickness of the ventricular wall. A catheter has a fiber optic connected at its handling end to a laser, and terminates at the insertable end of the catheter. A servomotor controls the advancing of the fiber to stop positions relative to the catheter. At each stop position another channel is created. An aiming beam aids in directing the channel forming fiber end to different desired channel positions.

14 Claims, 4 Drawing Sheets

MYOCARDIAL REVASCULARIZATION THROUGH THE ENDOCARDIAL SURFACE USING A LASER

This is a divisional of application Ser. No. 08/249,091, filed May 25, 1994, now U.S. Pat. No. 5,607,421.

BACKGROUND OF THE INVENTION

The present invention relates to a myocardial revascularization device and method for making channels in the inside of the heart ventricle to perfuse the myocardium.

Within this application several publications are references by arabic numerals within parentheses. Full citations for these and other references may be found at the end of the specification immediately preceding the claims. The disclosures of all of these publications in their entireties are hereby incorporated by reference into this application in order to more fully describe the state of the art to which this invention pertains.

It is well known that coronary artery disease is a pervasive disease afflicting many people in this country. Many of these people are treatable by coronary artery bypass surgery. However, alternative methods of myocardial revascularization are required for patients with coronary artery disease not amenable to coronary artery bypass. Investigators have used the $CO_2$ laser in arrested hearts to create transmural channels from the epicardial surface. The channels increase cardiac perfusion by shunting blood from the ventricle to myocardial sinusoids, and can endothelialize and remain patent indefinitely. In this approach, the energy is delivered from outside the ventricle, and the channels formed by the laser energy penetrate the full thickness through the ventricular wall.

SUMMARY OF THE INVENTION

It is an object of the present invention to provide an apparatus and method for myocardial revascularization to increase blood flow to the myocardium from the endocardium without using the native diseased coronary arteries.

It is an object of the present invention to provide an apparatus and method for myocardial revascularization to be used with patients having extensive coronary atherosclerosis in whom bypass surgery is not possible.

It is an object of the present invention to provide an apparatus and method for myocardial revascularization which avoids forming channels which penetrate the full thickness through the ventricular wall.

The present invention provides a method for cardiac revascularization using a transendocardial approach with an energy source such as a thulium-holmium-chromium: YAG (THC-YAG) laser. This approach can be used on a beating heart, concentrates its effects on the endocardium, which is the surface at highest risk for ischemia, and reduces potential risk of bleeding and aneurysmal formation associated with transmural channels.

According to one aspect of the invention, a method for myocardial revascularization of the heart in a patient is provided, comprising positioning a channel forming energy emitter inside the ventricle of the heart, and directing energy from the channel forming energy emitter toward the ventricular wall in an amount sufficient to form at least one channel in the ventricular wall into the myocardium to thereby increase blood flow from the endocardium to the myocardium. which identifies the location of the emitted energy from the channel forming energy emitter, locating an aiming beam energy detector outside the heart at a position adjacent a desired channel forming site, and wherein the step of directing energy from the channel forming energy emitter is performed after the aiming beam energy detector detects aiming beam energy to thereby indicate that the channel forming energy emitter is directed to the desired channel forming site. The desired channel forming site may be based on familiar epicardial anatomic landmarks, such as the epicardial branches of the coronary arteries.

According to another aspect, the present invention provides a method for myocardial revascularization of the heart in a patient, comprising entering the ventricle of the heart with a catheter having a lumen which houses a fiber which emits energy at a fiber end, locating the fiber end proximate to the ventricular wall, and emitting energy from said fiber end in an amount sufficient to form a channel in the ventricular wall into the myocardium to thereby increase myocardial blood flow from the endocardium to the myocardium.

A myocardial revascularization device is also provided in accordance with the invention, comprising a handpiece having at least one lumen, and having an insertable end and a handling end, a fiber for carrying energy from an energy source to a fiber end from which the energy is emitted, said fiber being received in one of said lumens, means for moving the fiber within the lumen to different stop positions, whereby the fiber end extends from the handpiece insertable end at different sites of a ventricular wall corresponding to said stop positions, and means for transmitting energy to said fiber end in an amount sufficient to form a channel in the ventricular wall into the myocardium at each of said sites, to thereby increase myocardial blood flow from the endocardium to the myocardium.

The present invention also provides a myocardial revascularization device, comprising a channel forming energy emitter means, for insertion into the ventricle cavity of a heart, for emitting energy to form at least one channel in the ventricular wall into the myocardium, an aiming beam energy emitter means for emitting an aiming beam which identifies the location of energy emitted from the channel forming energy emitter means, an aiming beam energy detector, for placing against the exterior of the heart, for detecting an aiming beam from the aiming beam energy emitter means, and means for energizing the channel forming energy emitter means in response to detection of an aiming beam by the aiming beam energy emitter. The aiming beam energy detector location may be selected on the basis of familiar epicardial anatomic landmarks, those being the epicardial branches of the coronary arteries.

These and other advantages will become apparent from the detailed description accompanying claims and attached drawing figures.

DETAILED DESCRIPTION OF THE PREFERRED EMBODIMENT

Figure 1:
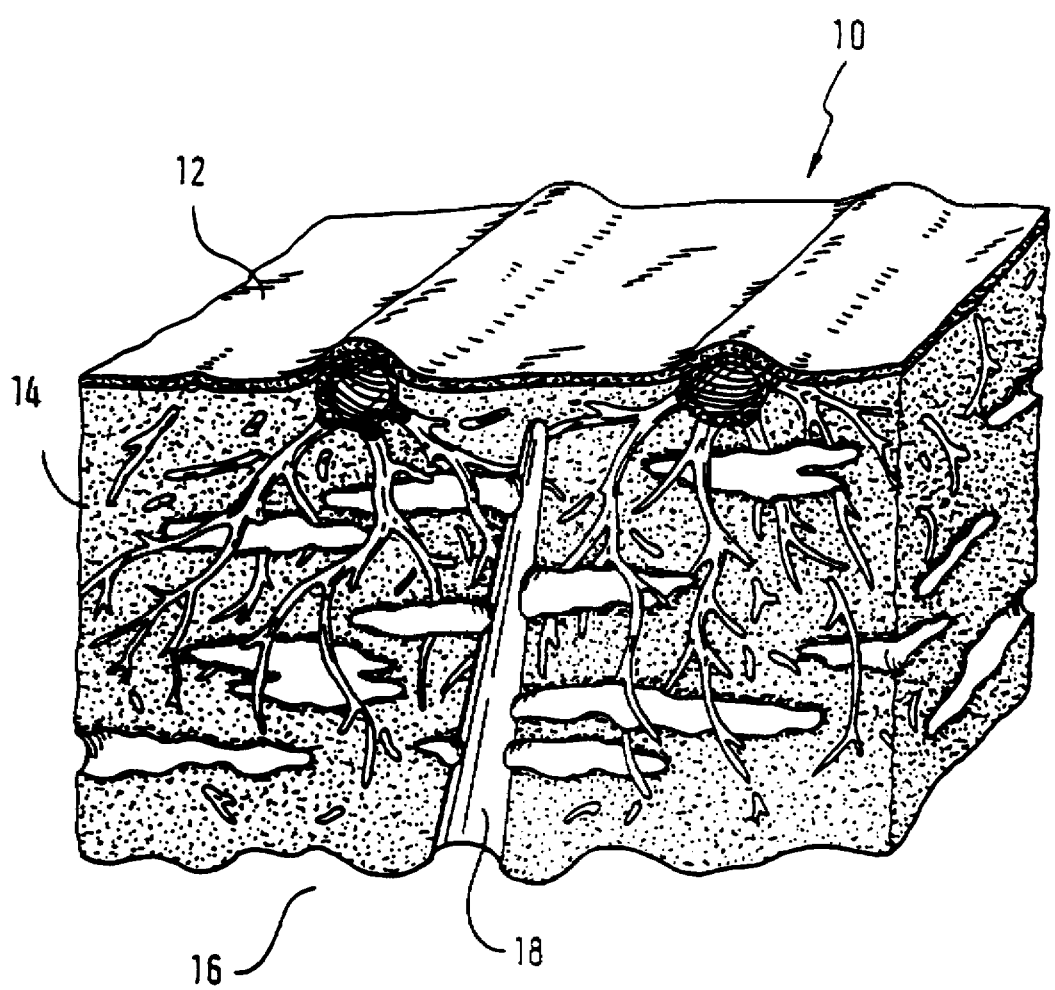
FIG. 1 is a cross-sectional view of a ventricular wall of a heart, showing the epicardium, myocardium, endocardium and a channel formed by a laser energy source according to the present invention.

According to one aspect of the invention, a method for myocardial revascularization of the heart in a patient is provided, comprising positioning a channel forming energy emitter inside the ventricle of the heart, and directing energy from the channel forming energy emitter toward the ventricular wall in an amount sufficient to form at least one channel in the ventricular wall into the myocardium to thereby increase blood flow from the endocardium to the myocardium. The energy emitter may be a laser. The steps of positioning and directing are preferably repeated to form channels at different sites in the ventricular wall.

The method preferably includes the steps of positioning an aiming beam energy emitter inside the ventricle of the heart, said aiming beam energy emitter having an emitting beam which identifies the location of the emitted energy from the channel forming energy emitter, locating an aiming beam energy detector outside the heart at a position adjacent a desired channel forming site. The channel forming site may be selected based on familiar epicardial anatomic landmarks, those being the epicardial branches of the coronary arteries. Further, the step of directing energy from the channel forming energy emitter is preferably performed after the aiming beam energy detector detects aiming beam energy to thereby indicate that the channel forming energy emitter is directed to the desired channel forming site.

The present invention also provides, in a patient, a method for myocardial revascularization of the heart, comprising entering the ventricle of the heart with a catheter having a lumen which houses a fiber which emits energy at a fiber end, locating the fiber end proximate to the ventricular wall, and emitting energy from said fiber end in an amount sufficient to form a channel in the ventricular wall into the myocardium to thereby increase myocardial blood flow from the endocardium to the myocardium. The fiber is preferably connected to a laser, so that the fiber end emits laser energy.

The steps of locating and emitting are preferably repeated to form channels at different sites in the ventricular wall. The step of locating preferably comprises advancing the fiber end relative to the catheter a selected distance, whereby channels are formed in the ventricular wall at said selected distances.

According to another aspect of the invention, a myocardial revascularization device is provided, comprising a handpiece having at least one lumen, and having an insertable end and a handling end, a fiber for carrying energy from an energy source to a fiber end from which the energy is emitted, said fiber being received in one of said lumens, means for moving the fiber within the lumen to different stop positions, whereby the fiber end extends from the handpiece insertable end at different sites of a ventricular wall corresponding to said stop positions, and means for transmitting energy to said fiber end in an amount sufficient to form a channel in the ventricular wall into the myocardium at each of said sites, to thereby increase myocardial blood flow from the endocardium to the myocardium.

The means for moving the fiber preferably comprises means for moving the fiber within the lumen to different stop positions each a selected distance apart. The means for transmitting energy preferably comprises a laser. The handpiece may include means for supplying medicinal fluid, and may have means for supplying the medicinal fluid under pressure. The medicinal fluid may be heparin, for example.

The means for moving the fiber may comprise servomotor means for moving the fiber a selected distance, and may comprise a foot switch to activate the servomotor means. The handpiece insertable end may include gripping means extending therefrom to grip a ventricular wall. The gripping means may comprise three suction cups.

According to another aspect of the invention, a myocardial revascularization device is provided, comprising a channel forming energy emitter means, for insertion into the ventricle cavity of a heart, for emitting energy to form at least one channel in the ventricular wall into the myocardium, an aiming beam energy emitter means for emitting an aiming beam which identifies the location of energy emitted from the channel forming energy emitter means, an aiming beam energy detector, for placing against the exterior of the heart, for detecting an aiming beam from the aiming beam energy emitter means, and means for energizing the channel forming energy emitter means in response to detection of an aiming beam by the aiming beam energy emitter. The aiming beam energy detector location may be selected on the basis of familiar epicardial anatomic landmarks, those being the epicardial branches of the coronary arteries. The aiming beam energy detector may comprise an array of detector elements.

The means for energizing may comprise control means for receiving an EKG signal from a patient. The channel forming energy emitter means preferably is energized in response to detection of an aiming beam by the aiming beam energy emitter and at a suitable time in the EKG cycle.

The myocardial revascularization device may comprise a magnetic element on the channel forming energy emitter means, and an electromagnet on the aiming beam energy detector, for electromagnetically coupling the channel forming energy emitter and detector, for stabilizing the channel forming energy emitter.

Referring now to the Figs., as shown in FIG. 1, a ventricle wall 10 has an epicardium 12, myocardium 14 and endocardium 16. A laser channel 18 is also shown, which extends into the ventricle wall 10 sufficiently to communicate with the myocardium layer but which does not extend entirely through the ventricle wall to and through the epicardium. The laser channel 18 was formed using the method and apparatus according to the present invention.

Figure 2A:
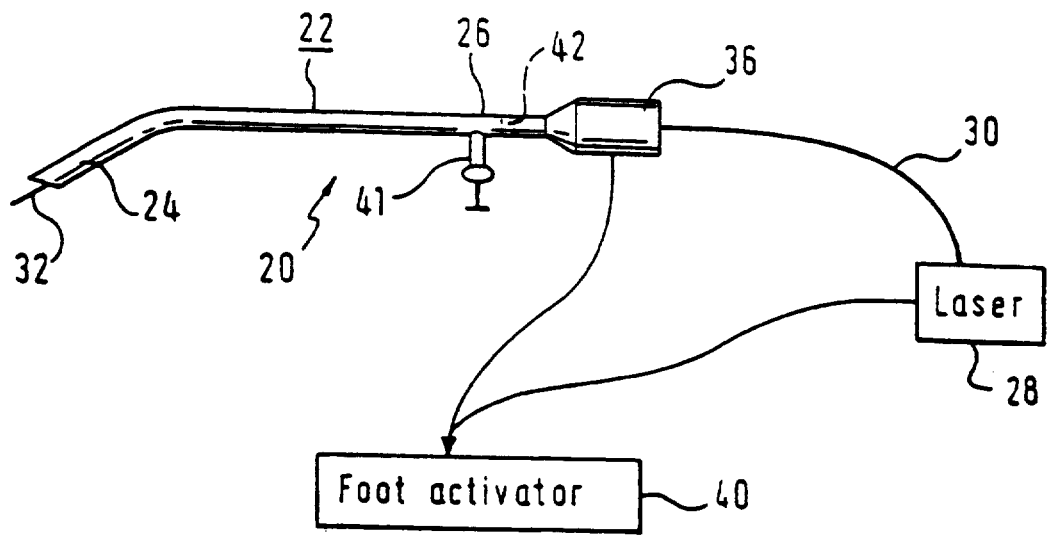
FIG. 2A is a myocardial revascularization device according to the invention.

FIG. 2A shows a myocardial revascularization device according to the present invention, which can be used to perform the method according to the present invention. The device 20 comprises a catheter 22 having at least one lumen, and having an insertable end 24, and an operating end 26 to be held by a physician. An energy source, such as a laser 28, which may be a THC:YAG laser, has connected to it a fiber optic 30, which may be one or more quartz fibers. The fiber optic 30 is received through the catheter lumen and is shown having an end 32 extending from the insertable end 24 of the catheter. A servomotor 36 serves to advance the fiber end 32 to stop positions spaced certain distances from each other. The spacing may be 1 to 10 mm. for example. The servomotor 36 is connected to and controlled by a foot activator 40. The foot activator is also connected to and controls the firing of the laser 28 when the fiber end is at the stop positions.

The device of FIG. 2A also has means for introducing medicinal fluid to the site, in the preferred form of heparin. The heparin is introduced under pressure as shown at 41 in FIG. 2A. A diaphragm 42 inside the catheter prevents the pressurized heparin from flowing out of the operating end 26 of the catheter.

Figure 2B:
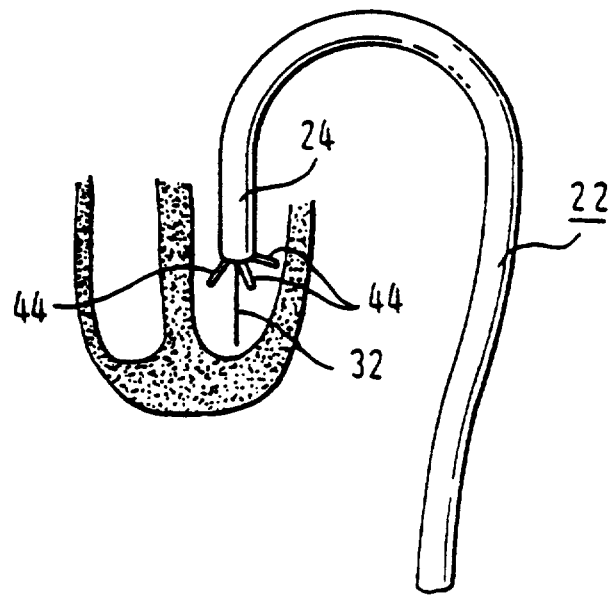
FIG. 2B shows in more detail gripping means such as suction cups on the insertable end of the catheter.

As shown in FIG. 2B the insertable end 24 of the device has gripping means extending therefrom in the form of three suction cups 44. These cups 44 provide a means to removably mount and stabilize the insertable end 24 to the inner ventricular wall, and serve as a tripod for the end 24, and the fiber end 32.

Figure 3:
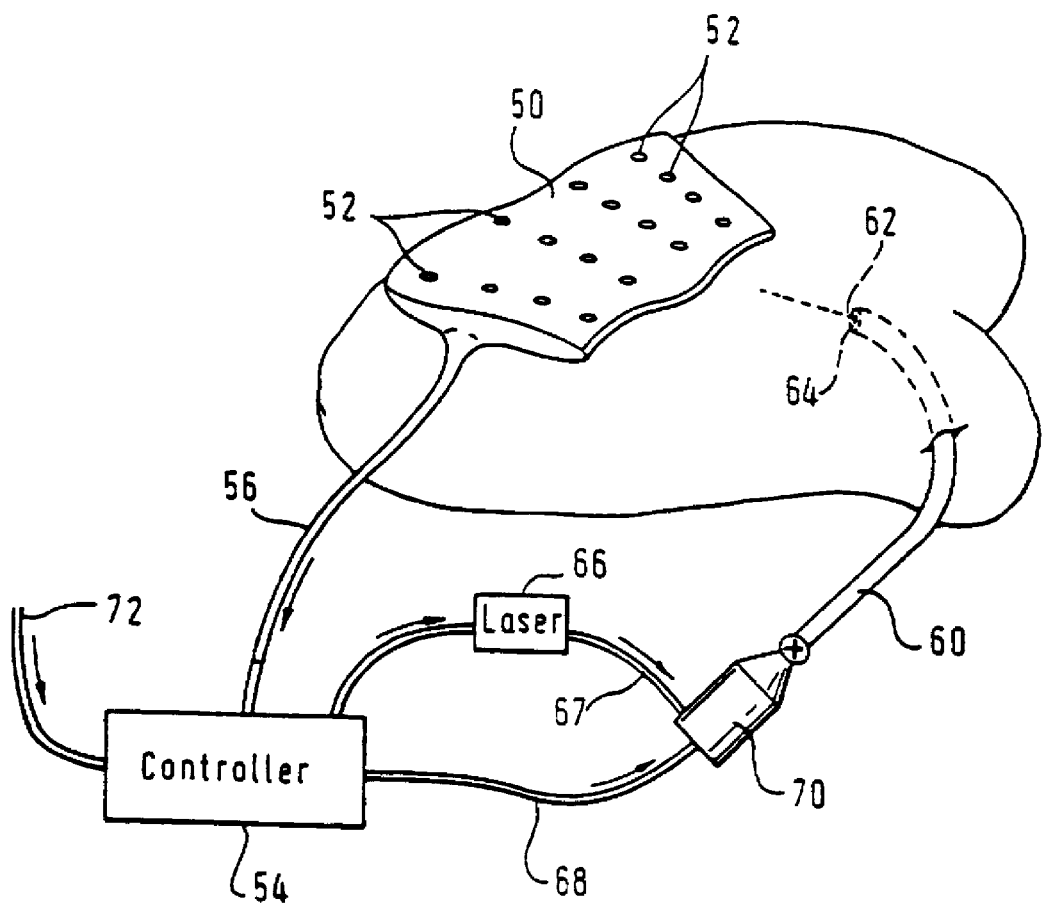
FIG. 3 shows an aiming grid to focus a transatrial laser at specific sites based on visible epicardial landmarks with the heart surgically exposed.

FIG. 3 shows an aiming grid and aiming beam arrangement useful for locating the desired target positions to fire the laser which creates the channels. This arrangement could be used in open chest surgery and can be used in a procedure as an adjunct to coronary bypass or other procedures.

This arrangement comprises an aiming grid 50 having sensors in the form of photodiodes 52 located in an array on a suitable sheet material. The grid 50 is adapted to be positioned inside of the thoracic cavity adjacent the heart outside the ventricular wall in which laser channels are desired. The grid 50 is connected to a controller 54 by cable 56.

A handpiece 60, having a shell of suitable plastic material, for example, houses an aiming bean source 62. The aiming beam source may be an 808 nm diode laser, but could also be other sources of electromagnetic, ultrasonic or magnetic energy. The aiming beam grid 50 has sensors compatible with and adapted to detect the energy source. The handpiece 60 may actually be a catheter having two lumens. Also disposed in the handpiece is a fiber optic end 64 for projecting a laser beam, similar to that of FIGS. 1 and 2. The fiber optic end 64 is connected, by a fiber optic 67 within the handpiece, to a laser 66 outside the handpiece. Control means to fire the laser 66 is provided in controller 66. The controller, by way of cable 68, also provides a means to control the servomotor 70, located in the base of the handpiece 60, for advancing the fiber optic end 64 to selected stop positions similarly as in FIGS. 1 and 2. The controller 54 is also connected to receive signals from a surface EKG by way of cable 72.

It is usually desired that only specific regions of the myocardium will be targets. The targets are based on the watershed areas of each of the coronary branches, such that a region poorly perfused by an occluded coronary branch would be a target, while an adjacent area might not. There are virtually no visual landmarks to provide a roadmap of the coronary branches when the ventricle is viewed from the inside and oven if there were, an optical system would be necessary to visually guide such a system. The coronary arteries are largely epicardial, and provide readily interpretable landmarks with which surgeons are quite familiar. The grid provides an arrangement for lining up the laser beam directly underneath the target, when the target is best identified by external landmarks.

The operation of the aiming beam grid arrangement is as follows. During open chest surgery, the grid 50 is positioned inside of the abdominal cavity adjacent the heart outside the ventricular wall in which laser channels are desired. The handpiece is inserted into the ventricular cavity and the aiming beam is energized.

When the aiming beam is sensed by the photodiode 52, indicating the proper location for a channel to be formed in the ventricular wall, the controller enables or automatically fires the laser 66. The controller also senses EKG signals and enables or automatically fires the laser only at the proper time in the heart cycle.

The handpiece is moved to different positions inside the ventricular cavity and when the aiming beam is sensed by another photodiode in the grid, the laser is enabled to create another channel in the ventricular wall. This process is continued until the desired number of channels is created. The controller may be provided with circuitry to determine whether a particular photodiode has previously sensed an aiming beau, so that when a channel has been created at that location, the laser will be prevented from being enabled at that location again, to thereby avoid firing the laser at a location where a channel has previously been created.

The controller may also be provided with means to detect the distance between the aiming beam source 62 (the end of the handpiece) and the grid 50, and the signal strength received. This computed distance and signal strength may be used to control the intensity of the laser energy used to create the channel and thus the size and depth thereof. The signal strength of the aiming beam received would indicate the ventricular wall thickness and dictate the channel depth desired.

The arrangement of FIG. 3 allows a physician to focus a retrograde transatrial laser at specific sites based on visible epicardial landmarks with the heart surgically exposed.

Figure 4:
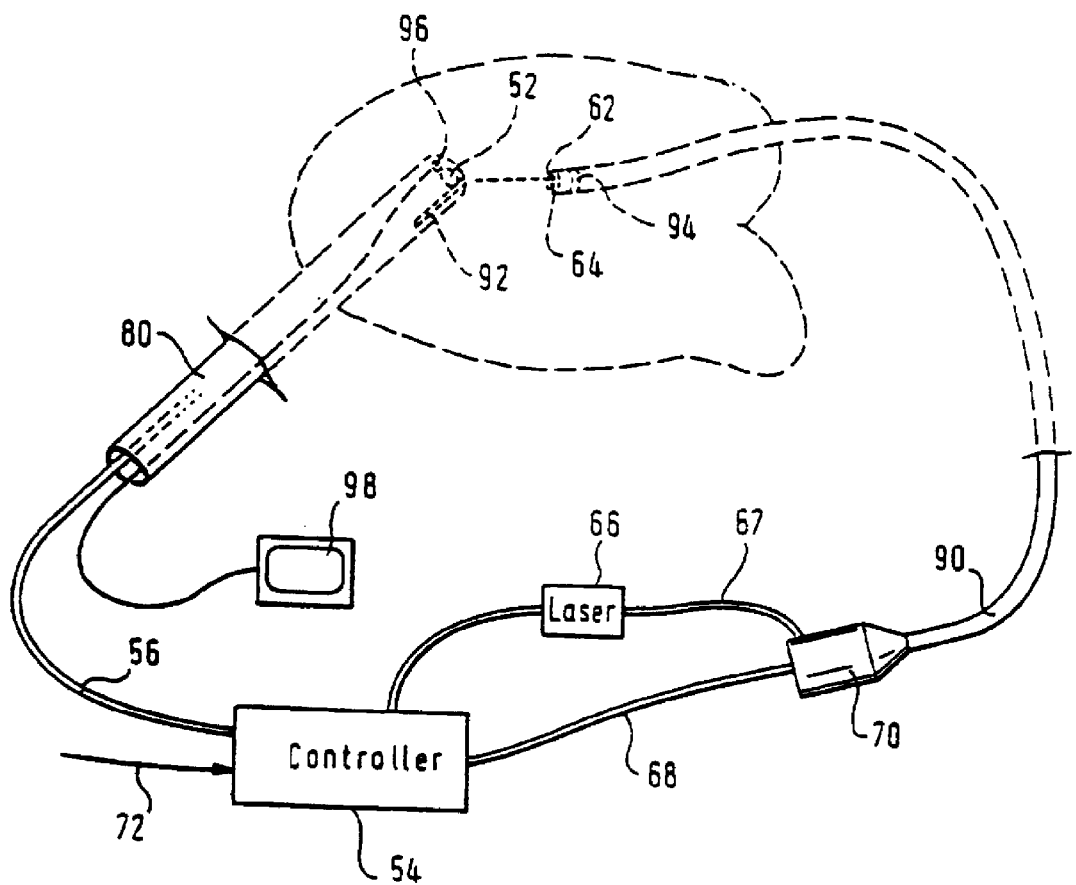
FIG. 4 shows a transthoracic aiming thorascope according to the invention.

FIG. 4 shows a transthoracic aiming thorascope according to the invention for focusing a percutaneously introduced laser catheter at specific sites based on epicardial landmarks. In this arrangement a single photodiode 52 is mounted at the end of a first handpiece 80 which is adapted to be inserted through adjacent ribs in the ribcage and positioned with its end against the exterior of the heart. The photodiode is connected to controller 54 by cable 50. The controller is also connected by cable 68 to a servomotor 70 in a second handpiece 90. A laser 66 is also connected to the controller 54, which controls the laser, and its output is through a fiber optic 67, which fiber optic extends throughout the length of the second handpiece and terminating at an end 64.

The second handpiece 90 also houses an aiming beam source 62, similar to that in FIG. 3. The second handpiece may be a catheter having two lumens as in the arrangement of FIG. 3. The controller 54 receives EKG signals similarly as in FIG. 3.

Similarly to the operation of the device of FIG. 3, the second handpiece 90 is inserted into the ventricular cavity. The aiming beam from source 62 projects from the second handpiece 90, and when the first handpiece 80 is aligned to have photodiode 52 receive the aiming beam from the second handpiece 90, the controller enables the laser 66 to fire and create a channel in the interior ventricular wall.

An electromagnet 92 may be mounted in the end of the first handpiece 80, and a metallic ring 94 may be mounted in the second handpiece 90. Magnetic force could be used to stabilize the first handpiece end against the endocardium directly opposite the aiming scope. The first handpiece 80, sometimes referred to an aiming scope, may be provided with appropriate imaging optics 96, connected to visual monitor 98, for direct visualization of the region. The details of this feature are well known to those skilled in the art.

An experiment conducted using the method according to the invention will now be described.

MATERIALS AND METHODS

The left anterior descending artery (LAD) of 18 dogs (10 laser, eight control) was ligated distal to the first diagonal, and the area at risk (AAR) was mapped with methylene blue dye. In laser animals, a catheter containing the laser fiber was passed through the left atrium, stabilized against the contracting left ventricular wall, and nontransmural channels (600 u diameter, about 4 channels/cm$^2$) were lasered through the endocardium (800 mJ pulses; frequency 3 Hz) until epicardial blanching was noted. Survivors (laser, 9/10; controls, 4/8) were sacrificed at six weeks, and the infarct size was outlined using triphenyltetrazolium chloride (TTC). Ventriculograms were done after the animals were killed by ligating the coronary arteries, clamping across the mitral and aortic valves, and instilling radiopaque dye into the ventricle.

RESULTS

The AAR was similar in both groups (12.7±2.3 cm$^2$ vs. 13.0±3.1 cm$^2$). Compared with controls at six weeks, laser-treated animals had smaller infarct size (3.67±0.32 cm$^2$ vs. 0.73±0.13 cm$^2$, P<0.02), and lower infarct-to-AAR ratio (0.26±0.05 vs. 0.06±0.02, P<0.02). Neither bleeding nor aneurysms occurred in any of the animals. Ventriculograms on control animals showed no perfusion of the free wall; laser-treated animals had dye-filled sinusoids in the free wall, filling through short channels originating from the endocardial surface.

DISCUSSION

Transmural channels created with a $CO_2$ laser increase myocardial perfusion in experimental models, and have been used clinically as an adjunct during coronary artery bypass. Postoperative ventriculography and radionuclide scans have demonstrated perfusion, through laser channels, of regions not revascularized through bypass grafts. The mechanism is thought to involve perfusion of the collateral network of myocardial sinusoids by flow entering the lasered channels from the ventricular cavity during systole. The channels remain open because carbonization associated with laser energy has been shown to inhibit lymphocyte, macrophage, and fibroblast migration. Thus, in contrast to channels created by needle acupuncture, laser channels heal more slowly and with less scar formation, which allows endothelialization and long-term patency. Bleeding from the epicardial site of penetration is usually controlled by clot formation.

To improve myocardial perfusion, the channels must allow communication between the ventricular cavity and myocardial sinusoids, but do not need to be transmural. In previous models, transmural channels were a consequence of the inability to deliver $CO_2$ laser energy through a flexible fiberoptic system, mandating application of the laser energy from the epicardial surface of the ventricle. The far-infrared (10.6 u) $CO_2$ laser has been used because of its ability to remove tissue precisely. The mid-infrared (2.15 u) THC:YAG laser has similar tissue effects because of a large absorption peak of water for light energy in the 2 u region. In addition, the wavelength of 2 u radiation is short enough to be effectively transmitted through low hydroxyl 600 u diameter quartz fibers. This feature permits application of laser energy from the endocardial surface of a beating ventricle, avoiding the need to create transmural channels from the epicardial surface.

Using this approach, the AAR in the experimental group was significantly decreased after the creation of laser channels, and after six weeks the laser animals had smaller infarcts, as measured by TTC staining. Laser-treated and control animals had similar initial AAR. In the laser-treated animals, but not in the controls, ventriculography at six weeks demonstrated noncoronary perfusion of myocardial sinusoids in the area at risk through short channels communicating with the ventricular chamber. There were no bleeding complications, aneurysms, or permanent arrhythmias.

In conclusion, laser energy can be transmitted through flexible quartz fibers to create myocardial channels from the endocardial surface in a beating heart. The channels improve perfusion acutely and remain patent for up to six weeks. This technique may be useful as an adjunct to coronary bypass or, with development of a delivery system, might permit percutaneous treatment of inoperable patients with diffuse coronary artery disease.

REFERENCES

1. Mirhoseini M, Shelgikar S, Cayton M M: New concepts in revascularization of the myocardium. Ann Thor Surg 45:415–420, 1988.

2. Okada M, Ikuta H, Shimizu K, et al: Alternative method of myocardial revascularization by laser: Experimental and clinical study. Kobe J Med Sci 32:151–161, 1986.

3. Hardy R l, Bove K E, James F W, et al: A histologic study of laser-induced transmyocardial channels. Lasers Surg Med 6:563–573, 1987.

4. Oz M C, Treat M R, Trokel S L, et al: A fiberoptic compatible mid-infrared laser with $CO_2$ laser like effect: Application to atherosclerosis. J Surg Res 47(6):493–501, 1989.

5. Treat M R, Trokel S L, Reynolds, R D, et al: A preliminary evaluation of a pulsed 2.15 micron laser for endoscopic surgery Lasers Surg Med 8:322–326, 1988.

We claim:

1. A myocardial revascularization device, comprising:

a channel forming energy emitter means, for insertion into a ventricle cavity of a heart, for emitting energy to form at least one channel in a ventricular wall into a myocardium;

an aiming beam energy emitter means for emitting an aiming beam substantially parallel to emitted energy from the channel forming energy emitter means which identifies a location of energy emitted from the channel forming energy emitter means;

an aiming beam energy detector comprising sheet material having a plurality of detectors arranged in a grid, for placing against the exterior of the heart, for detecting an aiming beam from the aiming beam energy emitter means; and means for energizing the channel forming energy emitter means in response to detection of an aiming beam by the aiming beam energy detector.

2. The myocardial revascularization device according to claim 1, wherein the means for energizing comprises control means for receiving an EKG signal from a patient, and wherein the channel forming energy emitter means is energized in response to detection of an aiming beam by the aiming beam energy emitter at a suitable time in the EKG cycle.

3. The myocardial revascularization device according to claim 1, further comprising:

a magnetic element on the channel forming energy emitter means, and an electromagnet on the aiming beam energy detector, for electromagnetically coupling the channel forming energy emitter and detector, for stabilizing the channel forming energy emitter.

4. A myocardial revascularization device, comprising:

a handpiece having at least one lumen, and having an insertable end and a handling end;

a fiber for carrying energy to a fiber end from which the energy is emitted, said fiber being received in one of said lumens;

servomotor means, and controller means for controlling the servomotor means, for advancing the fiber within the lumen to a plurality of different stop positions spaced certain distances from each other as the fiber is advanced by said servomotor means within the lumen from one stop position to the next without retraction, each of said plurality of different stop positions being spaced between 1 and 10 mm from one another and defining positions to which the fiber is advanced, whereby the fiber end extends from the handpiece insertable end at different sites of a ventricular wall corresponding to each of said plurality of different stop positions; and laser means for transmitting said energy to said fiber in an amount sufficient to form a channel in the ventricular wall into a myocardium at each of said sites, to thereby increase myocardial blood flow from an endocardium to the myocardium.

5. The myocardial revascularization device according to claim 4, wherein the handpiece further comprises fluid application means for supplying fluid adjacent to said different sites of the ventricular wall.

6. The myocardial revascularization device according to claim 4, wherein the controller means for controlling the servomotor means comprises a foot switch.

7. The myocardial revascularization device according to claim 4, wherein the handpiece insertable end includes gripping means extending therefrom to grip a ventricular wall.

8. The myocardial revascularization device according to claim 7, wherein the gripping means comprises three suction application means for gripping the ventricular wall.

9. An elongated device for forming a channel in a ventricular wall, comprising:

an elongated catheter having at least one lumen extending therein, a distal end, a proximal end and a port in the distal end in fluid communication with the lumen;

an optical fiber, which is slidably disposed within the catheter lumen, having a proximal end and a distal end and being configured for transmitting laser energy from a laser energy source connected to the proximal end of the optical fiber through the optical fiber to the distal end thereof and emitting transmitted laser energy out of the distal end of the optical fiber; and servomotor means, and controller means for controlling the servomotor means, connected to the optical fiber for advancing the optical fiber within the catheter lumen to a plurality of stop positions placed certain distances from each other as the optical fiber is advanced by the servomotor means within the lumen from one stop position to the next without retraction, each of said plurality of stop positions being between 1 and 10 mm from one another and defining positions to which the fiber is advanced to extend the distal end of the optical fiber out the port in the distal end of the catheter a selected distance to direct laser energy emitted from the distal end of the optical fiber at the ventricular wall to form a channel therein.

10. The elongated device of claim 9 including means to hold the distal end of the elongated catheter at a desired location adjacent the region of the ventricular wall into which a channel is to be formed.

11. The elongated device of claim 10 wherein the means to hold the distal end of the elongated catheter is a means to grip the ventricular wall.

12. The elongated device of claim 11 wherein the means to grip the ventricular wall includes means for applying suction to the ventricular wall.

13. The elongated device of claim 12 wherein the controller means for controlling the servomotor means comprises a foot switch.

14. An elongated device for forming a channel in a patient's ventricular wall, comprising:

an elongated catheter having at least one lumen, an insertable end, a handling end and a port in the insertable end in fluid communication with the lumen;

an optical fiber with a proximal end and a distal end slidably disposed within the lumen of the catheter for transmitting laser energy from the proximal end to the distal end of the optical fiber from which the laser energy is emitted;

servomotor means, and controller means for controlling the servomotor means, connected to the optical fiber for advancing the optical fiber within the lumen to a plurality of stop positions spaced certain distances from each other as the optical fiber is advanced by the servomotor means within the lumen from one stop position to the next without retraction, each of said plurality of stop positions being between 1 and 10 mm from one another and defining positions to which the fiber is advanced, whereby the distal end of the optical fiber extends out the port in the insertable end of the catheter adjacent to the ventricular wall in which a channel is to be formed; and means connected to the optical fiber for transmitting laser energy to the proximal end of the optical fiber in an amount sufficient to emit laser energy from the distal end of the optical fiber to form a channel in the ventricular wall.

* * * * *